United States Patent
Dib et al.

(10) Patent No.: US 6,297,254 B1
(45) Date of Patent: Oct. 2, 2001

(54) METHOD FOR THE PREVENTION OR TREATMENT OF A MOTONEURON DISEASE

(75) Inventors: Michel Dib, Paris; Jean-Marie Stutzmann, Villecresnes, both of (FR)

(73) Assignee: Aventis Pharma S. A., Antony (FR)

( * ) Notice: Subject to any disclaimer, the term of this patent is extended or adjusted under 35 U.S.C. 154(b) by 0 days.

(21) Appl. No.: 09/727,131

(22) Filed: Nov. 30, 2000

Related U.S. Application Data
(60) Provisional application No. 60/183,643, filed on Feb. 18, 2000.

(30) Foreign Application Priority Data

Dec. 1, 1999 (FR) .................................................... 99 15139

(51) Int. Cl.[7] .......................... A61K 31/44; A61K 31/425
(52) U.S. Cl. ............................................. 514/288; 514/367
(58) Field of Search ..................................... 514/288, 367

(56) References Cited

U.S. PATENT DOCUMENTS 5,780,489  7/1998  Brooks .

FOREIGN PATENT DOCUMENTS

| 4240798 | 6/1993 | (DE) . |
|---|---|---|
| WO 99/34785 | 7/1999 | (WO) . |
| WO 00/30642 | 6/2000 | (WO) . |

OTHER PUBLICATIONS

Sanderink et al., Involvement of human CYPIA isoenzmes in the metabolism and drug interactions of riluzole in vitro., J. Pharma. and Exper. Ther., 282(3):1465–1472 (1997).

Martinet et al., Pharmacokinetics and metabolism of riluzole., Drugs of Today, 33(8):587–594 (1997).

Louvel et al., Therapeutic advances in amyotrophic lateral sclerosis., Trends in Pharma. Sci. 18(6):196–203 (1997).

*Primary Examiner*—Raymond Henley, III
(74) *Attorney, Agent, or Firm*—Irving Newman

(57) ABSTRACT

The present invention relates to a method for the prevention or treatment of a motoneuron disease with a combination of an ergoline chosen from nicergoline and lumilysergol and of riluzole or one of its pharmaceutically acceptable salts.

11 Claims, No Drawings

METHOD FOR THE PREVENTION OR TREATMENT OF A MOTONEURON DISEASE

CROSS-REFERENCE TO RELATED APPLICATIONS

This application claims priority to Provisional Application No. 60/183,643, filed Feb. 18, 2000, and claims foreign priority to French Patent Application No. 99/15139 filed Dec. 1, 1999.

The present invention relates to the combination of an ergoline, chosen from nicergoline and lumilysergol, and of riluzole or one of its pharmaceutically acceptable salts, the pharmaceutical compositions containing it and their use in the prevention and/or treatment of motoneuron diseases.

Riluzole is marketed for the treatment of amyotrophic lateral sclerosis. This compound is also useful as an anticonvulsant, an anxiolytic and a hypnotic (EP 50551), in the treatment of schizophrenia (EP 305276), in the treatment of sleep disorders and of depression (EP 305277), in the treatment of cerebrovascular disorders and as an anesthetic (EP 282971), in the treatment of spinal, cranial or craniospinal traumas (WO 94/13288), as a radiorestorative (WO 94/15600), in the treatment of Parkinson's disease (WO 94/15601), in the treatment of neuro-AIDS (WO 94/20103), in the treatment of mitochondrial diseases (WO 95/19170).

Nicergoline or (8β)-10-methoxy-1,6-dimethylergoline-8-methanol-5-bromonicotinate (Sermion®) exhibits in particular α-blocking properties, α2-adrenolytic properties (CARPENE C. et al., J. Pharmacol., 14, 57–66 (1983)), antiischemic properties (CAHN R. et al., Chem. Abstracts, 107, 228784x (1987); UEDAT et al., Chem. Abstracts, 118, 225224f (1993)), anticalcium properties (TAKAHASHI K. et al., Br. J. Pharmacol., 100, 705–710 (1990)), antioxidant properties (TANAKA M. et al., Neurosci. Let., 248, 67–72 (1998)), antithrombotic properties (Chem. Abstracts 105, 54314k (1986)). It enhances learning and memory capacity (Chem. Abstracts, 113, 52358u (1990); Chem. Abstracts, 111, 108396h, 1989; Chem. Abstracts, 109, 86208c, 1988; Chem. Abstracts, 106, 12788e, 1987; Chem. Abstracts, 115, 198237s, 1991).

Lumilysergol or 1,6-dimethyl-8β-hydroxymethyl-10α-methoxyergoline or 1-methyl-10α-methoxy-9,10-dihydrolysergol is one of the metabolites of nicergoline (F. ARCAMONE et al., Biochem. Pharmacol., 21 (16), 2205–2013 (1972)). This compound exhibits, like nicergoline but to a lesser degree, α1-adrenergic and 5HT1a serotoninergic properties. It is also useful as an intermediate for the preparation of nicergoline (patent FR 2,616,788). The combination of riluzole and nicergoline for the treatment of spacticity is described in WO 00/30642.

It is known that, in vitro, motoneurons cultured with no trophic factor die within 48 to 72 hours (AG. ESTEVEZ et al., J. Neurosci., 18 (3), 923–931 (1998) and 18 (10), 3708–3714 (1998)).

Moreover, neuronal death induced by trophic factor deprivation can be partially prevented when the motoneurons are cultured on monolayers of astrocytes or in the presence of a conditioned medium obtained from astrocytes. In addition, the production, by the astrocytes, of trophic activity for the motoneurons is stimulated by riluzole (H. PELUFFO et al., Neuroscience letters, 228, 207–211 (1997)).

It has now been found that the combination of riluzole or one of its pharmaceutically acceptable salts and of an ergoline chosen from nicergoline and lumilysergol acts synergistically and greatly increases the trophic activity secreted by the astrocytes. This association can thus be used in the prevention and/or treatment of motoneurone diseases.

Motoneuron diseases include in particular amyotrophic lateral sclerosis, progressive spinomuscular atrophy, infantile muscular atrophy, primary lateral sclerosis.

The general protocol used is described by H. PELUFFO et al., Neuroscience letters, 228, 207–211 (1997).

CULTURES ENRICHED IN MOTONEURONS

The cultures enriched in motoneurons are prepared using the centrifugation method described by R. L. SCHNAAR and A. E. SCHAFFNER, J. Neurosci., 1, 204–217 (1981) and modified by W. CAMU and C. E. HENDERSON, J. Neurosci. Methods, 44, 59–70 (1992). The motoneurons are plated, at a density of 2500 cells per 35 mm plate, on culture plates previously coated with laminin/ornithine according to the method of A. G. ESTEVEZ et al., J. Neurosci., 18 (3), 923–931 (1998). The cultures are then maintained in L15 medium (GIBCO BRL) containing sodium bicarbonate (22 mM), conalbumin (0.1 mg/ml), putrescine (0.1 mM), insulin (5 µg/ml), sodium selenite (31 nM), glucose (20 mM), progesterone (21 nM), penicillin (100 IU/ml) and streptomycin (100 µg/ml).

The motoneurons thus obtained are composed of large (25–30 µM) and homogeneous neurones with long branched neurites. More than 70% of the cells are immunoreactive for the p75 neurotrophin receptor and the markers Islet ½ for the spinal motoneurons. About 70% of the motoneurons die by apoptosis 24 hours after the plating if the culture is carried out in the absence of a trophic factor.

CULTURES OF SPINAL CHORD ASTROCYTES

The astrocytes are obtained from young one-day-old Wistar rats according to the method of R. P. SANETO and J. DE VELLIS, in Neurochemistry a practical approach (A. J. TURNER and H. S. St JOHN) IRL Press, Oxford-Washington DC, p27–63 (1987) which has been slightly modified (H. PELUFFO et al., Neuroscience Letters, 228, 207–211 (1997). The spinal chords are disected in a sterile manner, freed of the meninges and of the dorsal ganglia and cut before incubation at 37° C. for 25 minutes in PBS (phosphate buffer saline: 137 mM NaCl, 2.68 mM KCl, 6.45 mM $Na_2HPO_4$, 1.47 mM $KH_2PO_4$) to which 0.25% of trypsin was added. The enzymatic treatment is stopped by the addition of 10 ml of Dubelcco's modified Eagle's medium (DMEM) to which 10% of fetal calf serum (FCS) was added and the mechanical dissolution is completed using the end of a 1-ml pipette. The cells are collected by centrifugation and then plated at a density of $1.5-2 \times 10^6$ cells per 25 cm² of culture medium in DMEM to which 10% of FCS, 100 IU/ml of penicillin and 100 µg/ml of streptomycin were added. After 3 days in vitro, the cultures are fed daily. When a visible monolayer of cells is complete, the cultures are stirred for 48 hours at 250 rpm and the monolayers are treated with cytosine arabinoside ($10^{-5}$ M) for 48 hours. The monolayers of astrocytes thus obtained are maintained for 48 hours in culture medium and then amplified at a density of $2 \times 10^4$ cells/cm².

The monolayers of astrocytes show a purity of more than 98% determined by immunoreactivity for the glial fibrillary acidic protein (GFAP).

TREATMENT OF THE ASTROCYTES WITH THE TEST PRODUCTS

The treatment of the astrocytes with the test products is carried out in the following manner: ergoline is dissolved in absolute ethanol and riluzole in 0.01N HCl, sterilized by filtration and used immediately after preparation. The monolayers of astrocytes are exposed to the vehicle or to the solutions of the test products for 24 hours. This medium is used at a 10-fold dilution in fresh L15 medium (Dubelco). The monolayers of astrocytes are washed 3 times with DMEM and incubated with complete L15 medium. The conditioned astrocyte medium is taken up 24 hours later and centrifuged at 2000 g for 3 minutes and used immediately or stored at −70° C. for 2 weeks maximum without loss of trophic activity.

For the immunochemical labelling of the motoneurons, the cultures are fixed in ice-cold methanol for 15 minutes and then washed and the non-specific sites are blocked with 2% bovine serum albumen (BSA)+0.1% of triton X100 in PBS. The cultures are incubated successively with antibodies directed against the 200 kD subunits of neurofilaments (1:200 Amersham), biotinylated goat serum (1:125, Gibco) and streptavidin peroxidase (1:200 Gibco) for 60 minutes at room temperature.

COUNTING OF THE CELLS AND STATISTICAL ANALYSIS

The cells immunoreactive for the neurofilaments and exhibiting neurites which are longer than the diameters of the cells are considered as viable motoneurons.

The number of motoneurons is evaluated by counting the labelled cells in a surface area of 0.4–1 $cm^2$ under a microscope with a 200 times magnification. In all cases, the values are expressed as a percentage of the number of motoneurons present in the cultures maintained with trophic factors (BDNF). The experiments are carried out at least 3 times.

The statistical analyses are carried out using the Student test (t-test).

The results obtained are the following:
Effect of riluzole, nicergoline and lumilysergol alone and their combinations on the neurotrophic activity of the motoneurons which is produced by the spinal astrocytes:

| PRODUCTS | Motoneuronal survival in % |
|---|---|
| vehicle alone | 44 ± 1.41 |
| riluzole (0.1 $\mu$M) | 68.0 ± 3 |
| lumilysergol (0.1 $\mu$M) | 57.4 ± 3.53 |
| nicergoline (0.1 $\mu$M) | 44.5 ± 3.53 |
| riluzole 0.1 $\mu$M + nicergoline 0.1 $\mu$M | 79 ± 8.02 |
| riluzole 0.1 $\mu$M + lumilysergol 0.1 $\mu$M | 84.5 ± 2 |

These results demonstrate that the riluzole and nicergoline or riluzole and lumilysergol combinations synergistically stimulate the motoneuronal trophic activity produced by the monolayers of spinal astrocytes.

Riluzole can be prepared according to the method described in Patent EP50551.

As pharmaceutically acceptable salts of riluzole, there may be mentioned in particular the addition salts with inorganic acids such as hydrochloride, sulfate, nitrate, phosphate or organic acids such as acetate, propionate, succinate, oxalate, benzoate, fumarate, maleate, methanesulfonate, isethionate, theophyllineacetate, salicylate, phenolphthalinate, methylene-bis-β-oxynaphthoate or substitution derivatives of these derivatives.

Nicergoline can be prepared according to U.S. Pat. No. 3,228,943.

1,6-Dimethyl-8β-hydroxymethyl-10α-methoxyergoline can be prepared according to the method described in Patent FR 2,616,788.

The present invention also relates to the pharmaceutical compositions comprising the combination of riluzole or one of its pharmaceutically acceptable salts and of an ergoline chosen from nicergoline and lumilysergol in the pure state or in the form of a combination with one or more compatible and pharmaceutically acceptable diluents and/or adjuvants and/or optionally in combination with another pharmaceutically compatible and physiologically active product. The products which constitute the combination may be administered simultaneously, separately or spaced out over time so as to obtain the maximum efficacy of the combination.

As solid compositions for oral administration, use may be made of tablets, pills, powders (gelatin capsules, cachets) or granules. In these compositions, the active ingredients are mixed with one or more inert diluents, such as starch, cellulose, sucrose, lactose or silica, under an argon stream. These compositions may also comprise substances other than the diluents, for example one or more lubricants such as magnesium stearate or talc, a coloring, a coating (sugar-coated tablets) or a glaze.

As liquid compositions for oral administration, use may be made of pharmaceutically acceptable solutions, suspensions, emulsions, syrups and elixirs containing inert diluents such as water, ethanol, glycerol, vegetable oils or paraffin oil. These compositions may comprise substances other than the diluents, for example wetting products, sweeteners, thickeners, flavorings or stabilizers.

The sterile compositions for parenteral administration may be preferably solutions which are aqueous or non-aqueous, suspensions or emulsions. As solvent or vehicle, use may be made of water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. The sterilization may be performed in several ways, for example by aseptisizing filtration, by incorporating into the composition sterilizing agents, by irradiation or by heating. They may also be prepared in the form of sterile solid compositions which may be dissolved at the time of use in sterile water or any other injectable sterile medium.

The compositions for rectal administration are suppositories or rectal capsules which contain, in addition to the active product, excipients such as cocoa butter, semisynthetic glycerides or polyethylene glycols.

The present invention also relates to the use of the combination of riluzole or one of its pharmaceutically acceptable salts and of an ergoline chosen from nicergoline and lumilysergol for the preparation of a medicament particularly useful in the prevention and/or treatment of motoneurone diseases and in particular amyotrophic lateral sclerosis, progressive spinomuscular atrophy, infantile muscular atrophy, primary lateral sclerosis.

The invention also relates to the method of preventing and/or of treating motoneurone diseases and in particular amyotrophic lateral sclerosis, progressive spinomuscular atrophy, infantile muscular atrophy, primary lateral sclerosis which consists in administering to the patient a combination of riluzole or one of its pharmaceutically acceptable salts and of an ergoline chosen from nicergoline or lumilysergol either simultaneously or separately or spaced out over time.

The doses depend on the desired effect, the duration of the treatment and the route of administration used; they are generally from 50 mg to 200 mg per day for riluzole and 30 mg to 120 mg per day for ergoline chosen from nicergoline or lumilysergol.

What is claimed is:

1. A pharmaceutical composition comprising a synergistically effective combination of an effective amount of a riluzole compound selected from riluzole and the pharmaceutically acceptable salts thereof and an effective amount of nicergoline or lumilysergol.

2. A pharmaceutical kit for the prevention or treatment of a motoneuron disease, said kit comprising a plurality of separate containers, at least one of said containers containing a riluzole compound selected from riluzole and the pharmaceutically acceptable salts thereof and at least another of said containers containing nicergoline or lumilysergol.

3. The kit of claim 2 wherein said riluzole compound is present in said container in an amount of from about 50 mg to 200 mg.

4. The kit of claim 2 wherein said lumilysergol is present in said other container in an amount of from about 30 mg to about 120 mg.

5. A method for the prevention or treatment of a motoneuron disease comprising contacting motoneurons in vitro with an effective amount of a riluzole compound selected from riluzole and the pharmaceutically acceptable salts thereof and an effective amount of an ergoline compound selected from the group consisting of nicergoline and lumilysergol.

6. A method for the prevention or treatment of a motoneuron disease comprising administering to a patient in need of such treatment an effective amount of a riluzole compound selected from riluzole and the pharmaceutically acceptable salts thereof and an effective amount of an ergoline compound selected from the group consisting of nicergoline and lumilysergol.

7. The method of claim 1 wherein said riluzole compound and said ergoline compound are administered simultaneously.

8. The method of claim 7 wherein said riluzole compound and said ergoline compound are administered sequentially.

9. The method of claim 8 wherein said administration of said compounds is spaced out over time.

10. The method of claim 6 wherein said riluzole compound is administered in an amount of from about 50 mg to 200 mg per day and said ergoline compound is administered in an amount of from about 30 mg to about 120 mg per day.

11. The method of claim 6 wherein said motoneuron disease is selected from the group consisting of amyotrophic lateral sclerosis, progressive spinomuscular atrophy, infantile muscular atrophy and primary lateral sclerosis.

* * * * *